(12) United States Patent
Beliveau

(10) Patent No.: US 8,555,413 B2
(45) Date of Patent: Oct. 15, 2013

(54) FLEXIBLE NOSE GUARD

(76) Inventor: Robert Gregory Beliveau, San Pedro, CA (US)

( * ) Notice: Subject to any disclaimer, the term of this patent is extended or adjusted under 35 U.S.C. 154(b) by 0 days.

(21) Appl. No.: 12/806,348

(22) Filed: Aug. 11, 2010

(65) Prior Publication Data
US 2012/0036607 A1    Feb. 16, 2012

(51) Int. Cl.
*A41D 13/00*    (2006.01)

(52) U.S. Cl.
USPC .................................................. 2/9

(58) Field of Classification Search
USPC ................ 2/9, 12, 14; 351/88, 136, 138
See application file for complete search history.

(56) References Cited

U.S. PATENT DOCUMENTS

| | | | | |
|---|---|---|---|---|
| 2,233,698 A | * | 3/1941 | Girouard | 2/206 |
| 2,363,557 A | * | 11/1944 | Schauweker | 2/9 |
| 5,416,923 A | * | 5/1995 | Peugh | 2/9 |
| 5,682,607 A | * | 11/1997 | Klein | 2/9 |
| 5,803,075 A | * | 9/1998 | Yavitz | 128/206.25 |
| 2006/0143766 A1 | * | 7/2006 | Ramsey | 2/15 |
| 2007/0250976 A1 | * | 11/2007 | Beliveau | 2/9 |

* cited by examiner

*Primary Examiner* — Katherine Moran

(57) ABSTRACT

In accordance with the present invention, a flexible nose guard is provided for protecting the nose from sunlight, the cold, and other outdoor elements. The nose guard is configured to cover the bridge and sides of a user's nose. In a preferred embodiment, the nose guard has a pentagonal body, resembling an upside-down pentagon with rounded corners. The top portion of the nose guard is substantially flat and sized to conform around the bridge of the nose. The bottom portion of the nose guard is a rounded corner or hyperbolic-shape configured to rest on top of the bridge of the nose. In a preferred embodiment, the nose guard is composed of an outer first layer of spandex having a sun protective factor, an intermediate second layer of open-cell foam, and a third, skin-facing layer of micro-suede material that contacts the skin. The nose guard offers different means of attachment to a user's face.

2 Claims, 12 Drawing Sheets

A

B

A

B

FLEXIBLE NOSE GUARD

BACKGROUND OF THE INVENTION

1. Field of Invention

This invention pertains to recreational nose guards designed to protect the nose from sunburn, frostbite, and other outdoor elements.

2. Background Information

Today's society is increasingly involved in outdoor sports and recreational activities yet concerns about avoiding skin cancer and other harmful effects of the sun are also greater than ever. In particular, there is a need among outdoor enthusiasts (e.g. mountaineers, cyclists, skiers) and workers to protect their nose from exposure to harmful Ultraviolet light and extreme cold, or other elements that can cause discomfort or skin damage. Importantly, there is a need for nose guards that are versatile and can be easily attached to the user's face and various types of eyewear, such as eyeglasses and goggles. Existing nose guards are limited in their attachment options, level of protection, level of user comfort, and/or adequate conformance to the user's nose. For example, many nose guards are pre-attached to goggles and require the wearer to use the whole apparatus. Moreover, existing nose guards are rigid, heavy, uncomfortable and/or difficult to use. Because existing nose guards are made of a non-breathable solid material such as vinyl or aluminum, the result is perspiration on the user's nose. Flexibility and comfort are often sacrificed for durability, and vice versa.

U.S. Pat. No. 3,346,875 to Weisberger (1967) discloses a nose and lip guard which detachably connects to each other and to a pair of eyeglasses. However, such a device is limited for use with eyeglasses and does not provide a comfortable fit or attractive appearance. U.S. Pat. No. 5,167,036 to Daprato (1992) discloses a nose protector configured to attach to eyeglasses, but consists of a guard and a complex system of cords for attaching the protective nose guard to the eyeglasses. Again, this device can only be used with eyeglasses and does not have an easy means of attachment. Similarly, the sun-protective nose guard disclosed in U.S. Pat. No. 5,717,992 to Tilghman (1998) can only be attached to eyeglasses via a loop strap, and does not provide a conforming fit due to a lack of flexibility. Breathability is also an important factor for reducing sweat and providing comfort, and minimizing the fogging of eyewear. U.S. Pat. No. 5,274,847 to Lauttamus (1994) discloses a sun-protective nose guard that attaches to eyeglasses or goggles using a strap that is looped over the bridge of the eyewear. However, the Lauttamus nose guard is described as being of tear-able and crease-able material, which limits the device to non-breathable materials such as paper or plastic. Moreover, existing nose guards do not provide alternative attaching means that allow them to be worn with eyeglasses, goggles, or without eyewear.

Thus, there is a need in the market for a sun-protective, breathable nose guard that attaches to the user's nose in various ways and is durable but comfortably conforms to the face for physical, outdoor activities. The face mask disclosed herein addresses these needs.

SUMMARY

In accordance with the present invention, a flexible nose guard is provided for protecting the nose from sunlight, the cold, and other outdoor elements. The nose guard is configured to cover the bridge and sides of a user's nose. In a preferred embodiment, the nose guard has a pentagonal body, resembling an upside-down pentagon with rounded corners. The top portion of the nose guard is substantially flat and sized to conform around the bridge of the nose. The bottom portion of the nose guard is a rounded corner or hyperbolic-shape configured to rest on top of the bridge of the nose. In a preferred embodiment, the nose guard is composed of an outer first layer of spandex having a sun protective factor, an intermediate second layer of open-cell foam, and a third, skin-facing layer of micro-suede material that contacts the skin. The nose guard offers different means of attachment to a user's face. On the surface of the nose guard's outer layer is a Velcro hook patch that facilitates attachment to a complimentary loop patch that can be affixed to the underside of the eyewear's nose bridge. For eyeglasses, a pair of small nose pad cuts in the upper center portion of the nose guard (on the left and right sides of the hook patch) are configured to receive the nose pads of the user's eyeglasses to further secure the face mask to the user's face. On the upper and lower perimeter of the hook patch is a fastening slit. The fastening slits are configured to provide added flexibility in the nose guard body and to receive a hook and loop fastening strap that is fastened around the bridge of the user's eyewear. The nose guard contains a thin, flexible reinforcing strip that can be bent or creased to keep the nose guard contoured to the shape of the user's nose. In a preferred embodiment the reinforcing strip is on the skin-facing layer of the nose guard and has an adhesive surface that provides for better attachment to the nose and keeps the nasal passages open for easier breathing by pulling outward on the nostrils. Alternatively, the adhesive can be provided on a separate adhesive strip on the skin-facing layer of the nose guard.

BRIEF DESCRIPTION OF THE DRAWINGS

The present invention, in accordance with preferred and exemplary embodiments, together with further objects and advantages thereof, is more particularly described in the following detailed description taken in conjunction with the accompanying drawings in which.

DETAILED DESCRIPTION

In a preferred embodiment, the nose guard of the present invention is constructed of three flexible, light, and durable layers: an outer first layer of fabric having a sun protective factor, an intermediate second layer of open cell foam material, and a third layer of micro suede or brushed nylon material that contacts the skin. The outer first layer is such that it can be embossed, debossed, or sublimated with a desired image or print logo/design. The outer layer may be composed of spandex (e.g. polyurethane-polyurea copolymer). The intermediate layer can be breathable foam such as open-cell foam or perforated closed-cell foam (e.g. airprene). The third layer of micro-suede has a breathable, wicking effect that allows greater air exchange and acts against the discomfort and eyewear fogging caused by moisture buildup. The layers can be joined via a thermoforming process and preferably cut via laser cutting or comparable method to provide well-sealed edges that are resistant to de-lamination. The resulting nose guard material can be repeatedly used and washed. For example, the micro-suede layer can first be flame-bonded to the spandex layer, with the foam layer sandwiched in between, followed by thermoforming. The result is a light, flexible, durable and more breathable nose guard that is superior to those existing in the market (e.g. plastic, metal, or neoprene). However, the nose guard of the present invention could be comprised of only one, two, or any number of material layers while keeping with the teachings of the invention. For example, in an alternate embodiment, the nose guard could be comprised of a single layer of neoprene, vinyl webbing or silicone.

Although, certain materials and manufacturing processes are disclosed herein, other comparable or suitable materials and methods may be employed, as known in the art, to carry out the invention. It should also be understood that the nose guard disclosed herein can be made in different sizes to suit various users, and the dimensions of the nose guard can be modified while keeping with the spirit of the invention.

Figure 1:
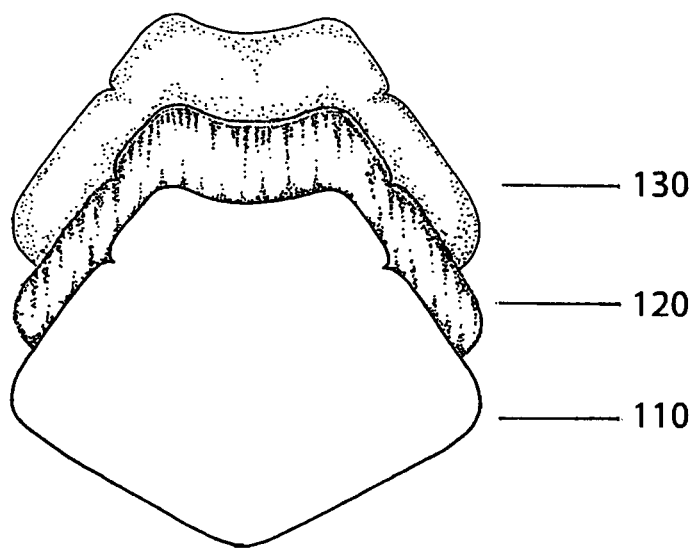
FIG. 1 illustrates the layers of the nose guard of the present invention.

FIG. 1 illustrates the layers of the nose guard of the present invention as described above. In an exemplary embodiment, the nose guard 100 is preferably constructed of three flexible, light, and durable layers: an outer first layer 110 having a sun protective factor, an intermediate second layer 120 of open cell foam material, and a third layer 130 of micro suede or brushed nylon material that contacts the skin. The outer first layer 110 is such that it can be embossed, debossed, or sublimated with a desired image or print logo/design, for example, as shown in FIG. 2B. The outer layer 110 may be composed of spandex (e.g. polyurethane-polyurea copolymer). The intermediate layer 120 can be breathable foam such as open-cell foam or perforated closed-cell foam (e.g. airprene). The third layer 130 can be a micro-suede with a breathable, wicking effect that allows for greater air exchange and acts against the discomfort caused by perspiration. The layers can be joined via a thermoforming process and preferably cut via laser cutting or comparable method to provide well-sealed edges that are resistant to de-lamination. For example, the micro-suede layer can first be flame-bonded to the spandex layer, with the foam layer sandwiched in between, followed by thermoforming.

Figure 2:
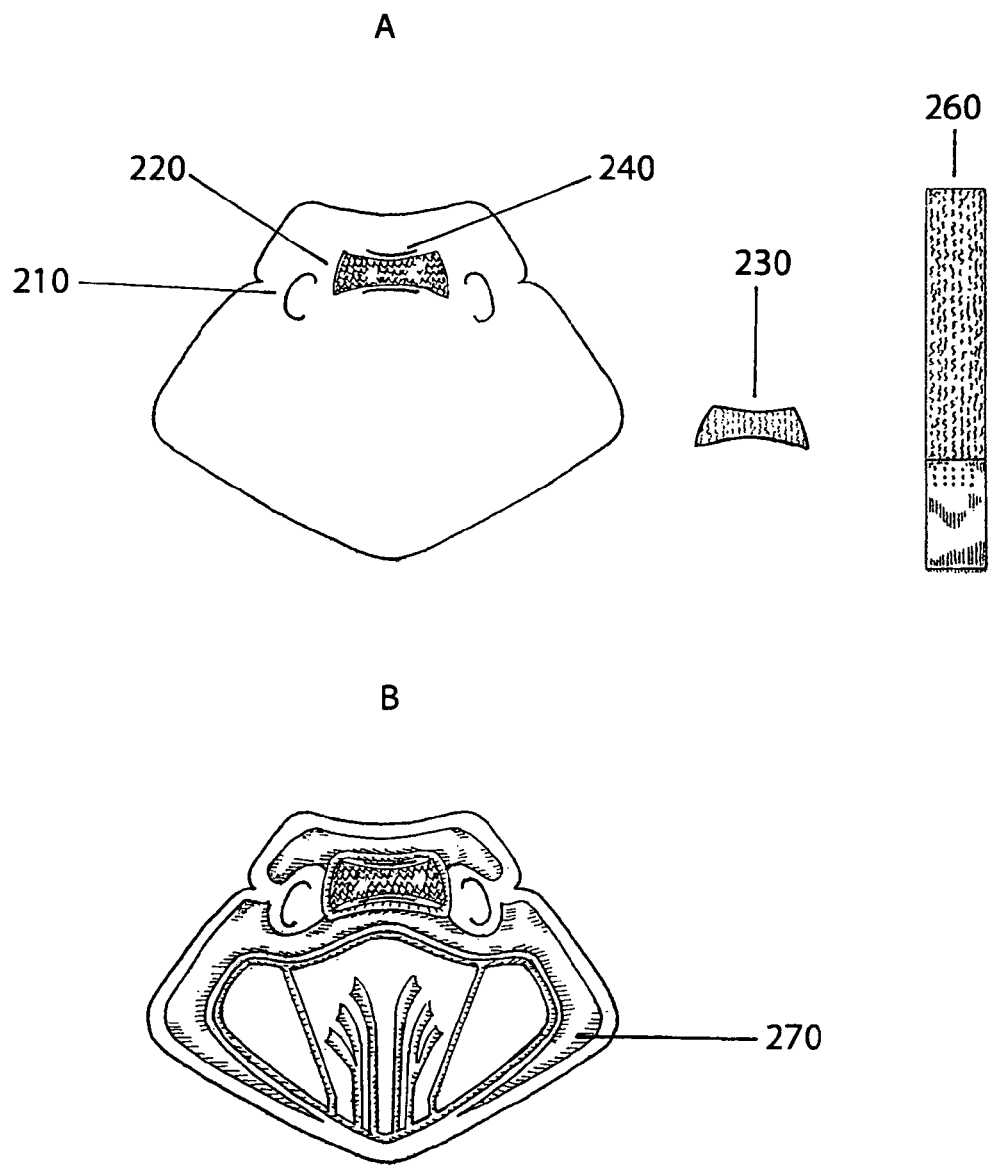
FIG. 2A illustrates the nose guard of the present invention having a pair of nose pad cuts, a pair of fastening slits, a hook patch, loop patch, and fastening strap for eyewear attachment.
FIG. 2B illustrates the nose guard with surface embossments.
Figure 10:
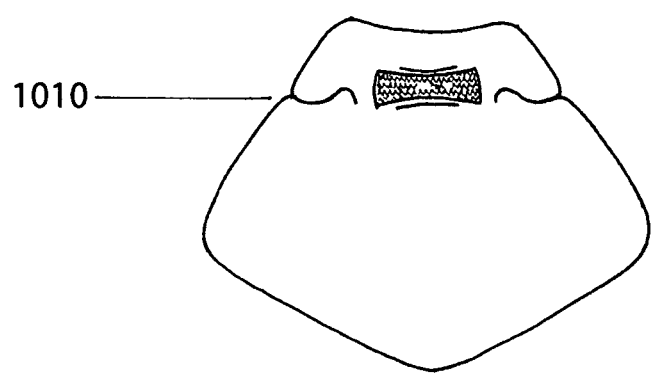
FIGS. 10A-B illustrate the nose guard of the present invention with "S"-shaped nose pad cuts.
Figure 10:
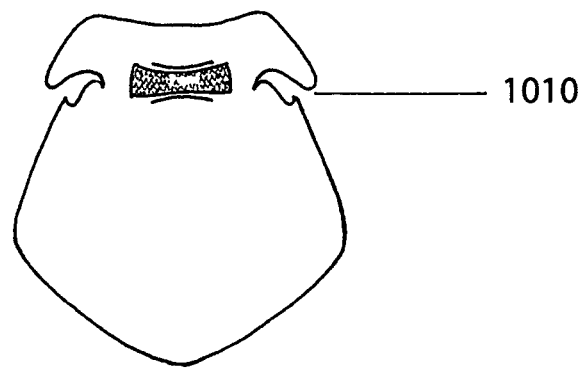

FIGS. 2A-B illustrate front views of the nose guard of the present invention, which comprises a pair of nose pad cuts 210, hook patch 220, loop patch 230, fastening slits 240, and fastening strap 260, which provide various means of attaching the nose guard to the user's eyewear. In the embodiment shown in FIG. 2, the nose pad cuts are "C"-shaped. However, the nose pad cuts may take other shapes to receive the nose pads of a user's eyeglasses, such as the "S"-shaped nose pad cuts shown in FIG. 10 (FIG. 10B shows the nose guard being bent, which opens the "S"-shaped nose pad cuts to receive eyeglass nose pads). The nose guard of FIG. 2A features a flat, plain surface while the embodiment shown in FIG. 2B contain surface embossments 270. The benefit of surface embossments and ridges is that the nose guard can be given more or less flexibility in certain directions to provide for a better fit to the user's nose. Also, the raised ridges provide padding for additional protection from outdoor elements as well as physical impact. Loop patch 230 contains an adhesive backing for attachment to various surfaces. Hook patch 220 is composed of Velcro "hook" fabric that is suited attach with the Velcro "loop" fabric of loop patch 230. The Velcro strap 260 contains a portion of hook fabric at one end, with the remaining length of the strap being loop fabric. The hook and loop materials are preferably a low-profile, micro-Velcro fabric such as that produced by 3M.

Figure 3:
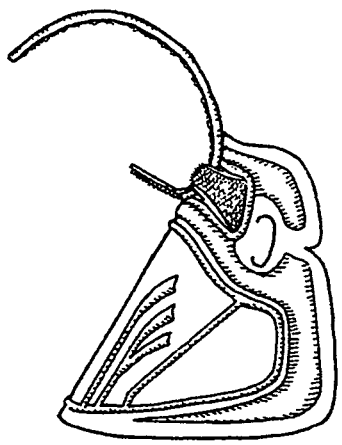
FIG. 3 illustrates the nose guard of the present invention with the fasting strap inserted through the fastening slits.
Figure 4:
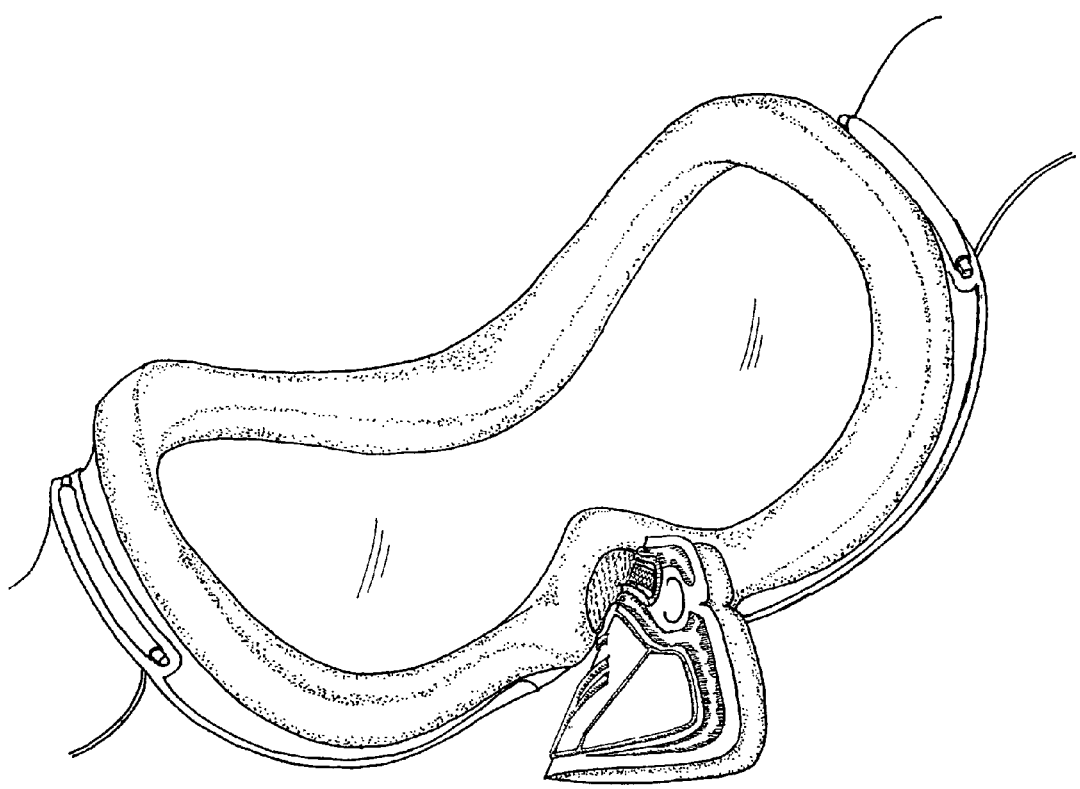
FIG. 4 illustrates the nose guard of the present invention attaching to goggles via hook and loop patches.
Figure 5:
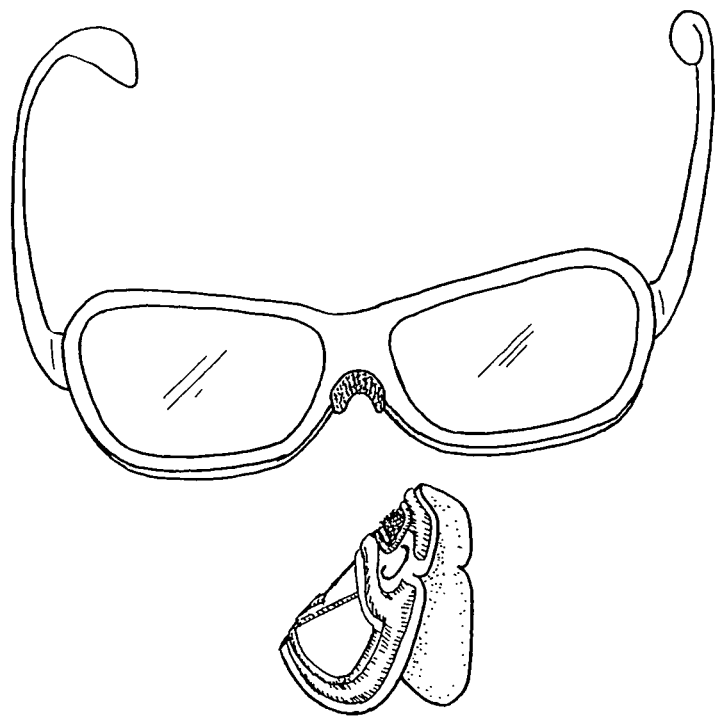
FIG. 5 illustrates the nose guard of the present invention attaching to eyeglasses via hook and loop patches.
Figure 6:
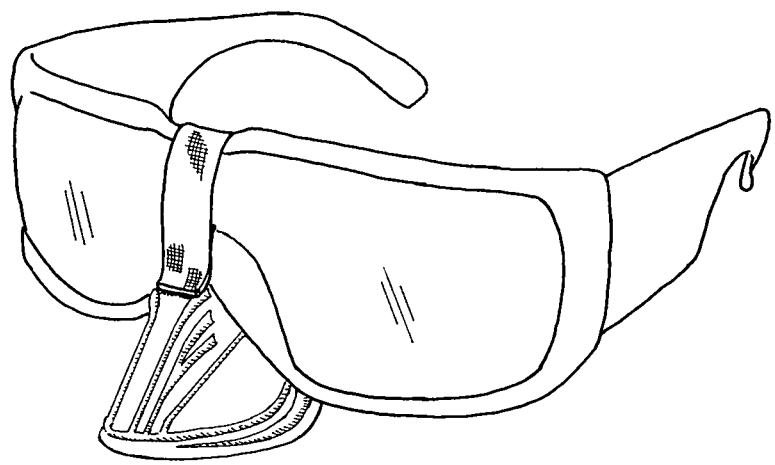
FIG. 6 illustrates the nose guard of the present invention attaching to eyeglasses via a fastening strap.
Figure 7:
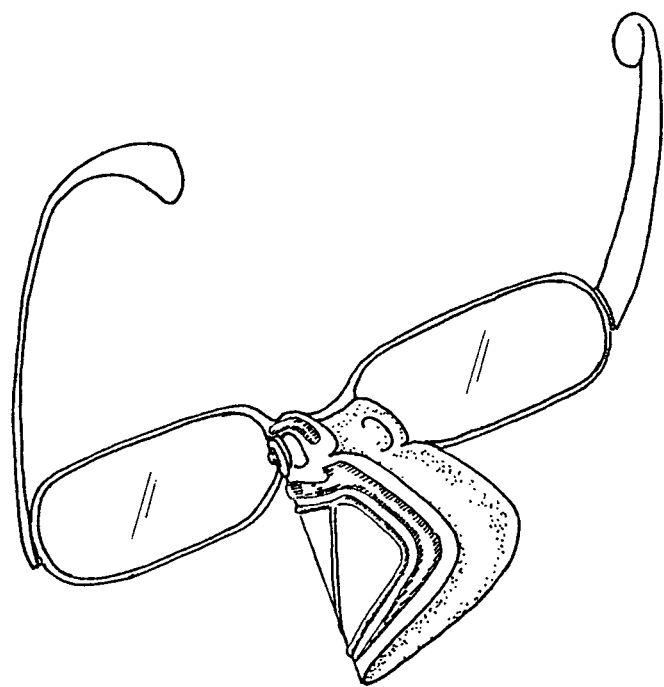
FIG. 7 illustrates the nose guard of the present invention attaching to eyeglasses via "C"-shaped nose pad cuts.
Figure 9:
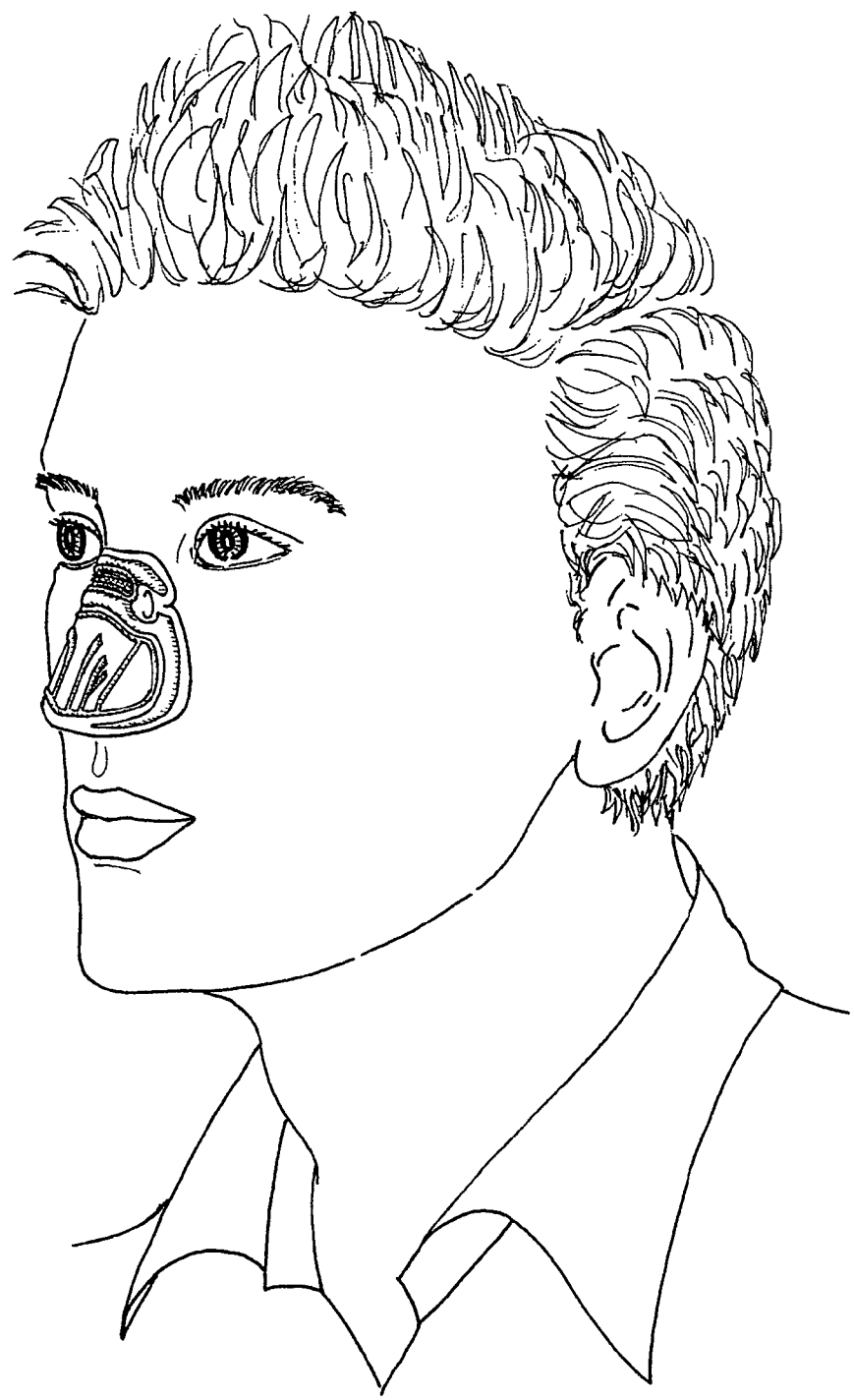
FIG. 9 illustrates the nose guard of the present invention being worn by a user via the adhesive reinforcing strip and without attachment to eyewear.
Figure 11:
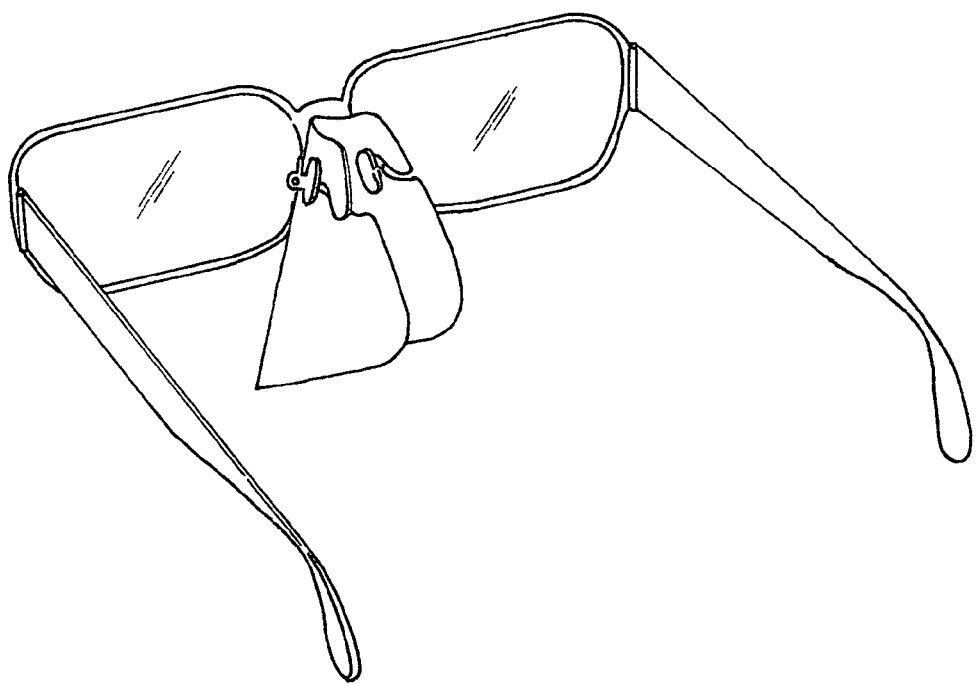
FIG. 11 illustrates the nose guard of the present invention attaching to eyeglasses via "S"-shaped nose pad cuts.

To further secure the nose guard to the user's face, three mechanisms allow the user to optionally secure the nose guard to their eyewear. First, if wearing ski-type goggles or eyeglasses, the user can affix loop patch 230 to the underside of the eyewear nose bridge and then bring hook patch 220 in contact with loop patch 230 as shown in FIGS. 4 and 5. Alternatively, the goggle liner itself may be composed of essentially loop-like material such that it can attach to hook patch 220 without the need for applying loop patch 230. Second, when wearing eyeglasses with nose pads, the user can insert the nose pads through the nose pad cuts 210 as shown in FIGS. 7 and 11. Third, if wearing eyeglasses without nose pads, or as an alternative to using the nose pad cuts 210, the fastening strap 260 can be put through the fastening slits 230 and around the bridge of the eyeglasses as shown in FIGS. 3 and 6. Either of these three methods secures the nose guard to the user's eyewear. FIG. 9, discussed below, shows a preferred embodiment of the nose guard that also gives the user the option of wearing the nose guard without attachment to any eyewear.

Figure 8:
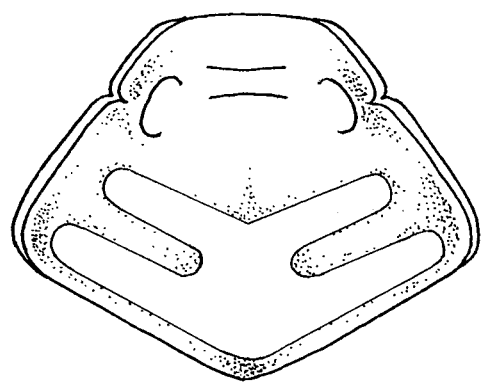
FIG. 8 illustrates the nose guard of the present invention having an adhesive reinforcing strip on the skin-facing layer.
Figure 12:
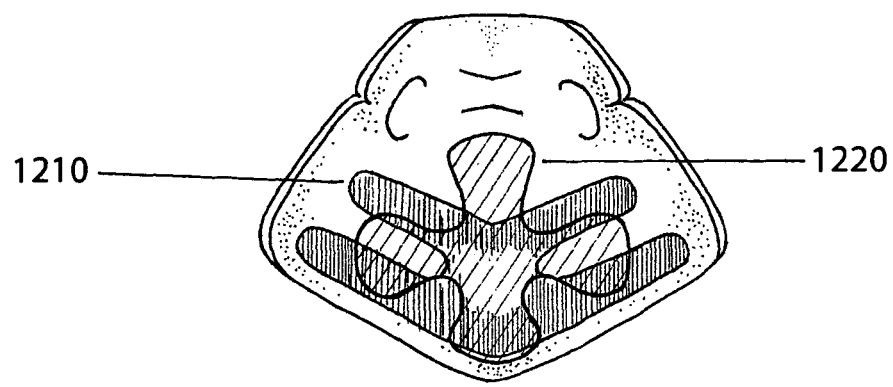
FIG. 12 illustrates the nose guard of the present invention having a reinforcing strip and adhesive strip on the skin-facing layer.

FIG. 8 shows a preferred embodiment of the present invention, which features a thin reinforcing strip affixed to the third layer (skin-facing side) of the nose guard. In an alternate embodiment, the reinforcing strip can be embedded within the nose guard and not visible to the user, i.e. between the first and second, or second and third, layers. The reinforcing strip is made of a flexible material that can be bent or creased to keep the nose guard portion of the mask contoured to the shape of the user's nose. While the reinforcing strip can take various shapes, it should run laterally (horizontally) from one side the nose guard to the other in order to provide structural support to the nose guard (and allow the nose guard to be contoured to the user's nose. The reinforcing strip is preferably made of a polymeric film such as polyester. Examples of suitable polyester films known in the art include Mylar (polyethylene terephthalate), DuraLar, and silicone. Alternatively, the reinforcing strip can be made of a thin strap of metal (e.g. aluminum). The reinforcing strip should be thin enough to be flexible, light, and have a low profile, but thick enough to provide some structure to the nose guard. For example, the thickness of the reinforcing strip can be approximately 0.005 inches. In one embodiment, the reinforcing strip can be lined with an adhesive film that sticks to the user's nose. This allows the nose guard to be worn without attachment to eyewear as shown in FIG. 9. Moreover, the combination of the adhesive and the natural restoring force of the bent nose guard causes the user's nostrils to be pulled outward, which opens the nostril passage and allows the user to breathe easier. The improved breathing is particularly advantageous during physical activities such as running, hiking, biking, manual labor, or other strenuous outdoor activities. Alternatively, an adhesive strip that is separate from the reinforcing strip can be utilized as shown in FIG. 12. The advantage of using a separate adhesive strip is that the adhesive can take on any shape as opposed to being limited to the surface of the reinforcing strip.

While there have been described herein what are considered to be preferred and exemplary embodiments of the present invention, other modifications of the invention shall be apparent to those skilled in the art from the teachings herein. It is therefore desired to be secured, in the appended claims all such modifications as fall within the spirit and scope of the invention.

What is claimed is:

1. A nose guard comprising:
    a flexible body configured to cover the bridge and sides of a user's nose;
    a pair of nose pad cuts, located on an upper center portion of the nose guard, configured to receive a pair of nose pads found on a user's eyewear, wherein the nose pad cuts comprise a pair of "S"-shaped cuts that begin within the nose guard body and continue to an outer edge of the nose guard to form an opening in the nose guard body, such that the "S"-shaped cuts are configured to receive the nose pads of a user's eyewear by sliding said nose pads into the opening and along the "S"-shaped cuts;
    a hook patch, located on an upper center portion of the nose guard, configured to attach to a user's eyewear;
    a detachable eyewear-fastening strap having a hook fabric on one end and a loop fabric on an opposite end, the hook and loop fabrics forming a reversible bond when brought into contact;
    a pair of fastening slits located immediately above and below the hook patch, said slits configured to receive the eyewear-fastening strap; and
    a thin reinforcing strip that facilitates shape retention and conformance to the user's nose.

2. A nose guard comprising:
    a flexible body configured to cover the bridge and sides of a user's nose;
    a pair of nose pad cuts, located on the an upper center portion of the nose guard, configured to received the nose pads of a user's eyewear, wherein the nose pad cuts comprise a pair of "S"-shaped cuts that begin within the nose guard body and continue to an outer edge of the nose guard to form an opening in the nose guard body, such that the "S"-shaped cuts are configured to receive the nose pads of a user's eyewear by sliding said nose pads into the opening and along the "S"-shaped cuts;
    a hook patch, located on the upper center portion of the nose guard, configured to attach to a user's eyewear; and
    a detachable eyewear-fastening strap having a hook fabric on one end and a loop fabric at the other end, the hook and loop fabrics forming a reversible bond when brought into contact; and
    a pair of fastening slits located to the top and bottom of the hook patch, said slits configured to receive the eyewear-fastening strap.

* * * * *